United States Patent [19]

Martis et al.

[11] Patent Number: 5,670,176
[45] Date of Patent: Sep. 23, 1997

[54] AMINO ACID SOLUTIONS FOR TREATMENT OF PERITONEAL DIALYSIS PATIENTS

[75] Inventors: Leo Martis, Long Grove; Michael R. Jones, Hawthorne Woods, both of Ill.

[73] Assignee: Baxter International Inc., Deerfield, Ill.

[21] Appl. No.: 416,407

[22] Filed: Apr. 4, 1995

Related U.S. Application Data

[62] Division of Ser. No. 995,855, Dec. 22, 1992.

[51] Int. Cl.$^6$ ............... A61K 31/195; A61K 31/19; A61K 31/70; A61K 33/14
[52] U.S. Cl. ............... 424/663; 424/677; 424/678; 424/679; 424/680; 424/681; 424/682; 424/686; 424/717; 424/722; 514/23; 514/400; 514/419; 514/423; 514/556; 514/557; 514/561; 514/562; 514/564; 514/565; 514/567
[58] Field of Search ............... 424/663, 677–682, 424/686–688, 692–693, 696–697, 717, 722; 514/557, 562, 564, 567, 23, 400, 419, 423, 556, 561, 565; 604/29

[56] References Cited

U.S. PATENT DOCUMENTS

| | | | |
|---|---|---|---|
| 4,357,343 | 11/1982 | Madsen et al. | 514/400 |
| 5,589,197 | 12/1996 | Shockley et al. | 424/663 |

FOREIGN PATENT DOCUMENTS

| | | |
|---|---|---|
| 1 239 586 | 7/1988 | Canada . |
| 0 347 714 | 12/1989 | European Pat. Off. . |
| 82/03773 | 11/1982 | WIPO . |

OTHER PUBLICATIONS

Arfeen et al, The Nutritional/Metabolic and Hormonal Effects of 8 Weeks of Continuous Ambulatory Peritoneal Dialysis with a 1% Amino Acid Solution, Clin Nephrol, pp. 192–199 (1990).

Bruno et al, CAPD With Amino Acid Dialysis Solution: A Long Term Cross Over Study, Kidney Int., vol. 35, pp. 1189–1194 (1989).

Dommbros et al, Six–Month Overnight Intraperitoneal Amino–Acid Infusion in Continuous Ambulatory Peritoneal Dialysis (CAPD) Patients—No Effect on Nutritional Status, Peritoneal Dialysis International, vol. 10, pp. 79–84 (1990).

Jones et al, Amino Acid Solutions for CAPD; Rationale and Clinical Experience, Miner Electrolyte Metab, vol. 18, pp. 309–315 (1992).

Hanning et al, Effect of Amino Acid Containing Dialysis Solutions on Plasma Amino Acid Profiles in Children with Chronic Renal Failure, Journal of Pediatric Gastroenterology and Nutrition, vol. 6, pp. 942–947 (1987).

Kopple et al, Nutritional Effects of Intraperitoneal Amino Acids (AA) in Malnourished CAPD Patients, J Am Soc Nephrol, vol. 2, p. 362 (Abstract) (1991).

Oren et al, Effective Use of Amino Acid Dialysate Over Four Weeks in CAPD Patients, Periton Dial Bull, vol. 3, pp. 66–73 (1983).

Oreopoulos, Amino Acids as an Osmotic Agent (Instead of Glucose) in Continuous Ambulatory Peritoneal Dialysis, First International Symposium in CAPD, Paris; Excerta Medica, pp. 335–340 (1979).

Williams et al, Amino Acid Absorption Following Intraperitoneal Administration in CAPD Patients, Perit Dial Bull, pp. 124–130 (Date unknown).

Young et al, The Use of Amino Acid–Base CAPD Fluid Over 12 Weeks, Nephrol Dial Transpl, vol. 4, pp. 285–292 (1989).

Young et al, A Longitudinal Study of the Effects of Amino Acid–Based CAPD Fluid on Amino Acid Retention and Protein Losses, Nephrol Dial Transplant, pp. 1–7 (1989).

*Primary Examiner*—John Pak
*Attorney, Agent, or Firm*—Thomas S. Borecki; Charles R. Mattenson; Robert M. Barrett

[57] ABSTRACT

The present invention provides a dialysis solution that contains amino acids for treating and/or preventing malnutrition in a peritoneal dialysis patient. The amino acid composition is optimized to minimize metabolic acidosis while normalizing amino acid plasma profiles.

5 Claims, No Drawings

AMINO ACID SOLUTIONS FOR TREATMENT OF PERITONEAL DIALYSIS PATIENTS

This is a division of application Ser. No. 07/995,855, filed on Dec. 22, 1992.

BACKGROUND OF THE INVENTION

The present invention relates generally to peritoneal dialysis and solutions for same. More specifically, the present invention relates to providing nutrition to peritoneal dialysis patients.

Dialysis provides a method for supplementing or replacing renal function in certain patients. Principally, hemodialysis and peritoneal dialysis are utilized. Although dialysis provides in many cases life saving therapy, there are health issues that must be addressed in such patients.

In hemodialysis, the patient's blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semi-permeable membrane. The peritoneum is the membranous lining of the body cavity that due to the large number of blood vessels and capillaries, is capable of acting as a natural semi-permeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows the proper acid-base, electrolyte, and fluid balance to be returned to the blood. The dialysis solution is then simply drained from the body cavity through the catheter.

Unfortunately, malnutrition is a risk factor for morbidity and mortality in peritoneal dialysis patients. Accordingly, much recent focus has been directed to improving the nutritional status of such patients. See, Amino Acid Solutions for CAPD: Rationale and Clinical Experience, Michael Jones et al, *Mineral and Electrolyte Metabolism,* 1992, 18:309–315.

Because there is no standard definition of malnutrition, estimates of the prevalence of malnutrition in CAPD patients vary. These estimates typically indicate that approximately 40 to 50% of CAPD patients are mildly to severely malnourished.

A variety of factors contribute to malnutrition in this patient population. Many factors hinder dialysis patients from eating nutritious diets. These factors include: poverty; depression; loss of taste acuity; dietary restrictions that result in an unpalatable diet; and underdialysis. This problem is compounded with the patient's greater than normal need for dietary protein due to losses of amino acids and proteins into dialysate, intercurrent illness, vitamin and mineral deficiencies, and co-morbid conditions such as diabetes.

There are additional features peculiar to CAPD that can also predispose such patients to malnutrition. Two such features include: inadequate dialysis; and the chronic effects of continuous glucose load. In this regard, glucose is typically used as the osmotic agent in a peritoneal dialysis solution. Glucose is not an inert osmotic agent, but is a nutrient as well. Glucose can contribute as much as 12 to 34% of the total calorie intake in CAPD patients. There is evidence that appetite and therefore food intake decreases as a function of the longevity of CAPD treatment. This may be due at least partly to the effects of chronic glucose absorption from the peritoneum.

Because glucose provides caloric support, the malnutrition experienced by CAPD patients is not believed to be based on a calorie deficiency. Rather, it is believed that protein intake is most often inadequate.

Accordingly, one approach to improving nutritional status in peritoneal dialysis patients is to use amino acids in place of glucose in the dialysate. Although amino acids should improve plasma proteins and/or total body nitrogen, there are problems inherent in adding amino acids to the dialysis solution. Metabolic acidosis is a catabolic event that will occur when many amino acid solutions are administered through the peritoneum. Additionally, many amino acid solutions will not modify the plasma amino acid profiles of malnourished CAPD patients so that they are normal.

For example, in Arfeen, The Nutritional/Metabolic and Hormonal Effects of Eight Weeks of Continuous Ambulatory Peritoneal Dialysis With a One Percent Amino Acid Solution, *Clin Nephrol* 1990; 33:192–199, 7 non-diabetic patients with chronic renal failure were treated by CAPD. During the treatment, a 1% amino acid dialysis solution replaced two of the four dextrose peritoneal dialysis exchanges. The amino acid solution, although it improved the plasma amino acid profile, resulted in significant metabolic acidosis.

See additionally: Oren et al, Effective Use of Amino Acid Dialysate Over Four Weeks in CAPD Patients, *Periton Dial Bull* 1983; 3:66–73; Young et al, The Use of Amino-Acid Based CAPD Fluid Over 12 Weeks, *Nephrol Dial Transpl* 1989; 4: 285–292; Dombros et al, Six-Month Overnight Intraperitoneal Amino Acid Infusion in Continuous Ambulatory Peritoneal Dialysis (CAPD) Patients—No Effect on Nutritional Status, Periton Dial Int 1990; 10: 79–84; and Bruno, CAPD With an Amino Acid Dialysis Solution: A Long-Term Cross-Over Study, *Kidney Int,* 1989; 35:1189–1194. Some of the results of the experiments reported in these articles are set forth in Example No. 2 infra.

Accordingly, there is a need for an improved amino acid solution that can be administered to a peritoneal dialysis patient as a treatment for malnutrition.

SUMMARY OF THE INVENTION

The present invention provides a peritoneal dialysis solution that contains amino acids for treating and/or preventing malnutrition in a peritoneal dialysis patient. The amino acid composition is optimized to minimize metabolic acidosis. To the best of the inventors' knowledge, all previous attempts at creating amino acid peritoneal dialysis formulations that can correct malnutrition and normalize plasma amino acid profiles suffer the disadvantage of metabolic acidosis.

To this end, the present invention provides an amino acid peritoneal dialysis solution that includes, in an embodiment, approximately 1% of an amino acid composition that comprises, per 100 ml of solution, the following:

| Amino Acid | Conc. (mg %) |
| --- | --- |
| Leucine | 74–112 |
| Valine | 100–151 |
| Threonine | 47–71 |
| Isoleucine | 61–92 |
| Lysine. HCl | 55–83 |
| Histidine | 52–78 |
| Methionine | 32–48 |

-continued

| Amino Acid | Conc. (mg %) |
|---|---|
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 |
| Preferred Ratios | |
| Phenylalanine/Tyrosine | 1.3–3.0 |
| Acid generating/ Acid neutralizing | 1–2.2 |
| Essential/Total | 0.4–0.7 |

In an embodiment, the remaining composition of the solution will include a typical dialysis solution from which glucose, or other osmotic agent, has been removed. For example, the solution can include, in an embodiment: 120–150 mEq/L sodium; 80–110 mEq/L chloride; 0.0–45.0 mEq/L lactate; 0.0–45.0 mEq/L bicarbonate; 0.0–4.0 mEq/L calcium; and 0.0–4.0 mEq/L magnesium.

In an embodiment, a dialysis solution is provided including the amino acids: leucine; valine; threonine; isoleucine; lysine; histidine; methionine; phenylalanine; tryptophan; alanine; proline; arginine; glycine; serine; tyrosine; aspartate; and glutamate; wherein the methionine is present in an amount that is less than 48 mg per 100 ml of total solution, the ratio of phenylalanine/tyrosine is 1.3 to about 3.0 and the ratio of acid generating/acid neutralizing amino acids is 1 to about 2.2.

Methods for providing nutrition to peritoneal dialysis patients are also provided.

It is an advantage of the present invention to provide a dialysis solution, including an amino acid composition, that can normalize plasma essential amino acid profiles in a peritoneal dialysis patient.

An additional advantage of the present invention is that it provides an amino acid composition that can be administered through the peritoneum of a patient without the danger of metabolic acidosis.

Another advantage of the present invention is that it allows for 15% to 30% reduction in a daily glucose loading through the peritoneal.

Additionally, an advantage of the present invention is to provide an amino acid solution that can be used for treating malnutrition in peritoneal dialysis patients.

Still further, an advantage of the present invention is that it provides an amino acid composition that has a sufficient amount of branched chain amino acids to compensate for the reduced level of branched chain amino acids in most dialysis patients.

Furthermore, an advantage of the present invention is to provide an amino acid composition that has reduced amounts of phenylalanine and increased amounts of tyrosine to deal with the problems dialysis patients have in converting phenylalanine to tyrosine.

Moreover, an advantage of the present invention is to provide an amino acid composition having lower quantities of methionine to reduce the amount of acid generating amino acids.

Another advantage of the present invention is to provide an amino acid composition that includes aspartate and glutamate to neutralize the acids generated by acid generating amino acids.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides an amino acid composition that can be used to treat and/or prevent malnutrition in peritoneal dialysis patients. Pursuant to the present invention, a solution is provided that can be administered through the peritoneum that has an amino acid profile that is designed to: 1) correct malnutrition; 2) normalize the plasma essential amino acid levels of a peritoneal dialysis patient; and 3) not produce metabolic acidosis in the patient.

The amino acid composition is preferably provided in a concentration of less than approximately 1.6% (w/v) of the dialysis solution and in an embodiment as approximately 1.1% to about 1% (w/v) of the dialysis solution. Although it is believed that the amino acid solution should not be used in concentrations greater than 1.6%, there may be certain circumstances where such a solution is desired.

The amino acid composition is designed in an embodiment to be used in a typical dialysis solution as a replacement for the osmotic agent. For example, the amino acid composition can replace glucose in currently used dialysis solutions, for example, DIANEAL® PD2 or PD4. However, the amino acid composition can be used with a dialysis solution including an osmotic agent such as glucose.

In an embodiment, the amino acid solution is present as approximately 1.1% of the dialysis solution and comprises, per 100 ml of solution, the following:

| Amino Acid | Conc. (mg %) |
|---|---|
| Leucine | 74–112 |
| Valine | 100–151 |
| Threonine | 47–71 |
| Isoleucine | 61–92 |
| Lysine. HCl | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 |

Preferably the ratios of some of the amino acids are as follows:

| Phenylalanine/Tyrosine | 1.3–3.0 |
|---|---|
| Acid Generating/ Acid Neutralizing | 1–2.2 |
| Essential/Total | 0.4–0.7 |

As stated above, the amino acid solutions of the present invention can be used in a variety of dialysis solutions. In an embodiment, the dialysis solution includes: 120–150 mEq/L sodium; 80–110 mEq/L chloride; 0.0–45.0 mEq/L lactate; 0.0–45.0 mEq/L bicarbonate; 0.0–4.0 mEq/L calcium; and 0.0–4.0 mEq/L magnesium.

The amino acid dialysis solutions of the present invention provide many benefits and advantages over heretofore employed dialysis solutions. The amino acid dialysis solution has a higher proportion of branched chain amino acids.

This addresses the problem of low concentrations of branched chain amino acids in many peritoneal dialysis patients.

Additionally, the amino acid dialysis solution of the present invention has reduced amounts of phenylalanine. However, the dialysis solution has increased amounts of tyrosine. The conversion of phenylalanine to tyrosine is impaired in many peritoneal dialysis patients.

Acid generation is a problem with peritoneal administered amino acid solutions. Pursuant to the present invention, lower quantities of methionine are present in the amino acid solution to reduce the amount of acid generating amino acids. On the other hand, aspartic and glutamic acid are added to neutralize the acid generated by the acid generating amino acids of the dialysis solution.

Still further, pursuant to the present invention, an optimal ratio between the acid generating and acid neutralizing amino acids is provided. Preferably, the ratio is 1 to 2.2. The acid generating amino acids include lysine, arginine, and methionine. The acid neutralizing amino acids include aspartic and glutamic acids.

By way of example, and not limitation, in an embodiment of the present invention, the following amino acid composition is present at approximately 1.1% of the dialysis solution: Amino Acid mg/ml, wt %

| Amino Acid | mg/ml* | wt % |
| --- | --- | --- |
| Leucine | 93 | 8.45 |
| Valine | 135 | 12.27 |
| Threonine | 59 | 5.36 |
| Isoleucine | 77 | 7.00 |
| Lysine/HCl | 60 | 5.45 |
| Histidine | 65 | 5.91 |
| Methionine | 40 | 3.64 |
| Phenylalanine | 52 | 4.73 |
| Tryptophan | 25 | 2.27 |
| Alanine | 85 | 7.73 |
| Proline | 54 | 4.91 |
| Arginine | 75 | 6.82 |
| Glycine | 46 | 4.18 |
| Serine | 60 | 5.45 |
| Tyrosine | 30 | 2.73 |
| Aspartate | 72 | 6.55 |
| Glutamate | 72 | 6.55 |

*of solution per 100 ml

By way of example, and not limitation, an experimental analysis of the present invention will now be given.

EXAMPLE NO. 1

The purpose of this study was to evaluate the nutritional effectiveness of Dianeal® with a 1.1% amino acids solution of the present invention.

The amino acid solution used had the following approximate amino acid composition:

| Amino Acid | Conc. (mg) per 100 ml |
| --- | --- |
| Leucine | 102 |
| Valine | 139 |
| Threonine | 65 |
| Isoleucine | 85 |
| Lysine/HCl | 76 |
| Histidine | 71 |
| Methionine | 85 |
| Phenylalanine | 57 |
| Tryptophan | 27 |
| Alanine | 95 |
| Proline | 59 |
| Arginine | 107 |

-continued

| Amino Acid | Conc. (mg) per 100 ml |
| --- | --- |
| Glycine | 51 |
| Serine | 51 |
| Tyrosine | 30 |
| Aspartate | 0 |
| Glutamate | 0 |

All patients participating in the trial were hospitalized for 35 days, during which time each patient received a fixed diet containing 0.8 g/kg/day protein and 25–30 kcal/kg/day. The first 15 days represented the control period during which patients performed their usual CAPD regimen using Dianeal® containing glucose, manufactured by Baxter Healthcare Corporation, Deerfield, Ill. The treatment period encompassed the twenty days immediately following the end of the control period.

During the treatment period, patients received one or two CAPD exchanges of Dianeal® with 1.1% amino acids so as to provide the equivalent of a total protein intake between 1.1–1.3 g/kg of actual body weight. A total of 25 patients from five centers were enrolled in the trial and nineteen completed the protocol.

The demographic characteristics of the nineteen patients—the mean age and time on CAPD were 54.1 years (range: 26–74 years) and 2.18 years (range: 0.4–8.7 years), respectively. The pre-entry protein intake estimated from dietary history varied from 0.84 to 1.1 g/kg/day. The average nitrogen balance, adjusted for changes in body urea nitrogen was +0.55 g/day during control period and this increased to +1.87 g/day during the treatment period (p=0.0015).

Peritoneal uptake of amino acids from the dialysate on the first day of administration (day 16) ranged from 76±10% for lysine to 86±5% for methionine, with an overall mean value of 80% for all the amino acids. The percent uptake did not change with continued use of the amino acid solution, and the overall mean values on days 26 and 35 were 70 and 80%, respectively.

plasma Amino Acids Profile

Fasting pre-exchange plasma amino acid concentrations for day 16 (end of the control period) and day 35 (end of the treatment period) are shown in Table 1. For the purpose of comparison, plasma amino acids for a group of 29 normal subjects with a median age of 50 years are also shown in Table 1.

At day 16, the study patients had a plasma amino acid pattern typical of that reported in renal patients by other investigators. Specifically, concentrations of the branched-chain amino acids (isoleucine, leucine, and valine), tyrosine, serine, and the essential/nonessential, valine/glycine, add tyrosine/phenylalanine ratios were reduced compared to normal, and citrulline, and glycine/serine and citrulline/arginine ratios were increased. In general, the essential amino acids, with the exception of phenylalanine, were low or low-normal.

At the end of the treatment period (day 35) there were significant increases (p<0.05) in plasma concentrations of histidine, lysine, and valine and increases in total branched-chain amino acids and total essential amino acids. There were also increases in cystine and in the nonessential amino acids arginine and serine and a decrease in taurine. As can be seen in Table 1, treatment with the amino acid solution tended to move the fasting plasma amino acids toward a more nearly normal pattern.

Biochemical Data

Serum chemistries were measured at the beginning of the study (day 0), at the end of the control period (day 16), and at the end of treatment with amino acid solution (day 36). The following is a description of changes in the variables of relevance to nutritional status and the ones showing statistically significant changes during the treatment with amino acids solution:

Serum albumin tended to rise during the treatment period although the increase was not statistically significant. It was not expected that a significant change would be observed because of the long half-life of albumin (21 days) and the large extravascular albumin pool.

Serum transferrin, a circulating protein with a shorter half-life and smaller body pool, rose from 226 to 250 mg/dl (p=0.001).

Total $CO_2$ decreased from 25.33 to 21.32 mEq/l (p=0.001).

Blood urea nitrogen (BUN) decreased from 60.24 to 48.65 mg/dl (p=0.0001) during control period and rose to 77.16 mg/dl (p=0.0001) during the treatment period.

Serum inorganic phosphorous decreased from 5.61 to 4.79 mg/dl (p=0.0174) during the control period and decreased further to 3.85 mg/dl (p=0.006) during treatment with amino acids solution. The decline in serum phosphorus during the control period may have been due to better control of dietary phosphorus and better compliance with phosphate binders.

SUMMARY AND CONCLUSIONS

The clinical study was designed to evaluate the efficacy of Dianeal® with 1.1% amino acids in improving nutritional status of a group of malnourished CAPD patients. Efficacy criteria included evaluation of the amino acids solution in improving nitrogen balance. In addition, several other biochemical and clinical assessments were made during the course of the study to determine the safety and efficacy of the product.

The results of this multi-center clinical study establish the effectiveness of Dianeal® with 1.1% amino acids solution in improving nutritional status of malnourished CAPD patients. The lack of any clinically significant adverse reactions in this study along with long-term clinical experience with amino acids containing solutions in parenteral nutrition indicates that this product is safe for use in peritoneal dialysis patients.

| Amino Acid (umoles/l) | Day 16 | Day 35 | Normal Subjects (n = 29) |
|---|---|---|---|
| Histidine* | 63.5 ± 10.3 | 75.3 ± 12.8 | 88 ± 10 |
| Isoleucine | 57.2 ± 14.1 | 55.8 ± 10.8 | 64 ± 16 |
| Leucine | 85.6 ± 18.5 | 88.8 ± 20.8 | 127 ± 27 |
| Lysine* | 158.4 ± 34.6 | 173.4 ± 31.1 | 197 ± 38 |
| Methionine | 23.5 ± 10.5 | 22.9 ± 3.6 | 28 ± 5 |
| Phenylalanine | 56.0± 17.4 | 55.6 ± 15.9 | 56 ± 9 |
| Threonine | 117.7 ± 35.2 | 135.7 ± 40.3 | 155 ± 41 |
| Valine* | 139.8 ± 29.1 | 186.4 ± 42.4 | 232 ± 51 |
| Total Essential | 701.7 ± 114.2 | 794.4 ± 113.7 | 945 ± 160 |
| Cystine* | 56.0 ± 20.4 | 68.5 ± 23.1 | 61 ± 10 |
| Tyrosine | 33.81 ± 10.9 | 33.9 ± 7.7 | 62 ± 13 |
| Alanine | 386.8 ± 1362 | 414.2 ± 155.0 | 433 ± 116 |
| Arginine* | 81.1 ± 21.6 | 92.6 ± 18.9 | 99 ± 22 |
| Asparagine | 45.0 ± 11.4 | 45.2 ± 9.8 | 48 ± 13 |
| Aspartic Acid | 13.3 ± 6.2 | 14.2 ± 7.0 | 6 ± 3 |
| Citrulline | 91.1 ± 25.0 | 98.2 ± 28.7 | 39 ± 12 |
| Glutamic Acid | 51.1 ± 20.1 | 46.2 ± 25.9 | 46 ± 22 |
| Glutamine | 670.1 ± 138.9 | 660.0 ± 92.2 | 480 ± 133 |
| Glycine | 336.9 ± 109.2 | 317.7 ± 119.0 | 265 ± 118 |
| Ornithine | 51.1 ± 12.2 | 59.0± 15.1 | 66 ± 28 |
| Proline | 187.0 ± 44.8 | 205.2 ± 54.5 | 210 ± 65 |
| Serine* | 66.5 ± 18.0 | 70.7 ± 11.8 | 108 ± 24 |
| Taurine* | 67.1 ± 31.1 | 45.2 ± 19.5 | 48 ± 18 |
| Total Nonessential | 2048 ± 366.7 | 2068 ± 368.7 | 1850 ± 378 |
| Hydroxyproline | 36.1 ± 10.9 | 34.9 ± 12.6 | 16 ± 13 |
| Essential/Nonessential | 0.3 ± 0.1 | 0.4 ± 0.1 | 0.5 ± 0.1 |
| Valine/Glycine | 0.5 ± 0.3 | 0.7 ± 0.3 | 0.9 ± 0.1 |
| Tyrosine/Phenylalanine | 0.6 ± 0.1 | 0.6 ± 0.1 | 1.1 ± 0.2 |
| Glycine/Serine | 5.2 ± 1.7 | 4.5 ± 1.6 | 2.5 ± 0.9 |
| Citrulline/Arginine | 1.1 ± 0.3 | 1.1 ± 0.2 | 0.4 ± 0.1 |
| Total Branched Chain Amino Acids | 282.6 ± 57.2 | 331.0 ± 65.2 | 423 ± 90 |

*p < 0.05 (Day 16 vs. Day 35)

EXAMPLE NO. 2

Table II below is a comparison of serum bicarbonate from the different formulations and examples. The formulation of the present invention was tested pursuant to the protocol set forth in Example No. 1. The other formulations were tested as reported in the articles that are referenced by the first name author:

| Study Form Dosage | Oren Travasol® 1X1% | Dombros Travasol® 1X1% | Young 151' 1X1% | Bruno 151' 1X1% | Afreen 151' 2X1% | Example No. 1 Present Inv. 1X1.1% |
|---|---|---|---|---|---|---|
| BL | 23.8 ± 1 | 23.8 ± 1 | 24.6 | 23 ± 3 | 21.0 ± 0.6 | 25.8 ± 2.4 |
| Week 1 | 22.3 ± 1 | | | | | |
| Week 2 | 20.5 ± 1.4 | | | | 18 ± 0.7" | |
| Week 3 | 19.3 ± 3.7 | | | | | 23.6 ± 3.0 |
| Week 4 | 21.5 ± 2.4 | 23.0 ± 2.8 | | | 18 ± 1.1" | |
| Week 6 | | | | | 16 ± 0.7" | |
| Week 8 | | 24.0 ± 2.1 | 21.4 ± 2.4 | | 16 ± 07" | |
| Week 12 | | 23.0 ± 1.2 | 21.6 ± 1.6 | 19 ± 2" | | |
| Week 16 | | 23.4 ± 0.9 | 21.6 ± 1.3 | | | |
| Week 20 | | 23.8 ± 0.9 | 21.6 ± 1.3 | | | |
| Week 24 | 22.6 ± 1.3 | | 20 ± 2" | | | |
| Post | | | 24.7 ± 1.6 | 22 ± 1 | | |

BL equals base line bicarbonate blood level. 1×1% is one exchange per day at 1% amino acids. 2×1% means two exchanges at 1% amino acids. An asterisk indicates metabolic acidosis; the values are statistically significantly different from BL, $p<0.05$.

As noted in the study, TRAVASOL®, at one exchange, did not present any problems with respect to metabolic acidosis. However, TRAVASOL® is not nutritionally balanced and does not compensate or provide a sufficient nutrition to the patients to normalize plasma amino acid profile, and compensate for malnutrition in the patients. Accordingly, the table indicates that the only formulation that will normalize plasma essential amino acid profiles and compensate for the malnutrition of renal failure patients is the formulation of the present invention.

It should be noted that at 2×1.1%, the formulation of the present invention had the following results BL=24.6 ±1.5 and at week 3, 8.5±1.5*. IN order to correct the acidosis of two exchanges, preferably glutamic and aspartic acid are added. Additionally, methionine can be reduced.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutrition to a peritoneal dialysis patient comprising the steps of administering at least once a day a peritoneal dialysis solution that includes:

| Amino Acid | Conc. (mg) |
|---|---|
| Leucine | 74–112 |
| Valine | 100–151 |
| Threonine | 47–71 |
| Isoleucine | 61–92 |
| Lysine | 55–83 |
| Histidine | 52–78 |
| Methionine | 32–48 |
| Phenylalanine | 42–62 |
| Tryptophan | 20–30 |
| Alanine | 68–103 |
| Proline | 43–65 |
| Arginine | 60–113 |
| Glycine | 36–55 |
| Serine | 48–72 |
| Tyrosine | 20–35 |
| Aspartate | 55–83 |
| Glutamate | 55–83 | per 100 ml of solution, the ratio of phenylalanine/tyrosine ranging from about 1.3 to about 3.0, the ratio of basic amino acids/acidic amino acids ranging from about 1.0 to about 2.2.

2. The method of claim 1 wherein the solution includes:
120–150 mEq/L sodium;
80–110 mEq/L chloride;
0.0–45.0 mEq/L lactate;
0.0–45.0 mEq/L bicarbonate;
0.0–4.0 mEq/L calcium; and
0.0–4.0 mEq/L magnesium.

3. The method of claim 1 wherein the solution includes glucose.

4. The method of claim 1 wherein the solution is administered twice a day.

5. The method of claim 1 wherein the amino acids are present at less than or equal to 1.6 w/v of the total solution.

* * * * *

UNITED STATES PATENT AND TRADEMARK OFFICE
CERTIFICATE OF CORRECTION

PATENT NO. : 5,670,176

DATED : September 23, 1997

INVENTOR(S) : Leo Martis, et al.

It is certified that error appears in the above-identified patent and that said Letters Patent is hereby corrected as shown below:

Column 5, Line 24: delete "Amino Acid mg/ml, wt %"

Column 6, Line 39: delete "plasma" and insert --Plasma--

Column 6, Line 49: delete "add" and insert --and--

Table 1, Lysine* at Day 35 column: delete "173.4" and insert --173.8--

Table 1, Total Essential at Normal Subjects column: delete "160" and insert --150--

Table 1, Tyrosine at Day 16 column: delete "33.81" and insert --33.8--

Table 1, Aspartic Acid at Day 16 column: delete "6.2" and insert --5.2--

Table 1, Ornithine at Day 16 column: delete "51.1" and insert --51.6--

Table 1, Total Nonessential at Day 16 column: delete "366.7" and insert --356.7--

Table 2, Week 2 at Afreen 151' 2X1% column: delete " " " and insert --'--.

Table 2, Week 4 at Afreen 151' 2X1% column: delete " " " and insert --'--.

Table 2, Week 6 at Afreen 151' 2X1% column: delete " " " and insert --'--.

Table 2, Week 8 at Afreen 151' 2X1% column: delete " " " and insert --'--.

Table 2, Week 12 at Bruno 151' 1X1% column: delete " " " and insert --'--.

Table 2, Week 20 at Dombros Travasol® 1X1% column: delete "0.9" and insert --1.3--

Table 2, Week 20 at Young 151' 1X1% column: delete "21.6±1.3"

Table 2, Week 24 at Oren Travasol® 1X1% column: delete "22.6±1.3"

UNITED STATES PATENT AND TRADEMARK OFFICE
CERTIFICATE OF CORRECTION

PATENT NO. : 5,670,176
DATED : September 23, 1997
INVENTOR(S) : Leo Martis, et al.

It is certified that error appears in the above-identified patent and that said Letters Patent is hereby corrected as shown below:

Table 2, Week 24 at Dombros Travasol® 1X1% column: insert --22.6±1.3--

Table 2, Week 24 at Young 151' 1X1% column: delete "20±2"

Table 2, Week 24 at Bruno 151' 1X1% column: insert --20±2--

Column 9, Line 34: delete "8.5" and insert --18.5--

Signed and Sealed this

Ninth Day of June, 1998

BRUCE LEHMAN

Attest:

Attesting Officer

Commissioner of Patents and Trademarks